United States Patent [19]

Mason et al.

[11] Patent Number: 5,782,780
[45] Date of Patent: Jul. 21, 1998

[54] METHOD OF FORMING A CONTOURED ORTHOTIC MEMBER

[75] Inventors: Bradley R. Mason, Olivenhain; Jeffrey T. Mason, Escondido, both of Calif.

[73] Assignee: Breg, Inc., Vista, Calif.

[21] Appl. No.: 695,196

[22] Filed: Jul. 31, 1996

[51] Int. Cl.$^6$ ...................................................... A61F 5/00
[52] U.S. Cl. ...................................... 602/6; 602/7; 602/26
[58] Field of Search ............................... 602/5–8, 16, 26, 602/20, 23; 425/177, DIG. 110

[56] References Cited

U.S. PATENT DOCUMENTS

| | | | |
|---|---|---|---|
| 2,060,001 | 11/1936 | Attwood et al. | 602/6 X |
| 2,958,325 | 11/1960 | Claydon et al. | 602/6 X |
| 3,942,522 | 3/1976 | Wilson | 602/6 X |
| 4,161,175 | 7/1979 | Bentele | 602/6 X |
| 4,407,276 | 10/1983 | Bledsoe | 602/16 |
| 4,768,502 | 9/1988 | Lee | 602/6 X |
| 4,776,326 | 10/1988 | Young et al. | 602/16 |
| 4,941,480 | 7/1990 | McLean et al. | 602/16 |
| 5,405,312 | 4/1995 | Jacobs | 602/5 |
| 5,409,451 | 4/1995 | Daneman | 602/21 |
| 5,503,622 | 4/1996 | Wehr | 602/5 |
| 5,624,386 | 4/1997 | Tailor et al. | 602/16 |
| 5,693,007 | 12/1997 | Townsend | 602/26 |

FOREIGN PATENT DOCUMENTS

22 61821  2/1993  United Kingdom .

*Primary Examiner*—Linda C. Dvorak
*Attorney, Agent, or Firm*—Rodney F. Brown

[57] ABSTRACT

A method of forming an orthotic member conforming to a contour of a body is provided, wherein a flat member having a substantially two-dimensional shape and constructed from a pliable material is bent into a substantially three-dimensional shape approximating the contour of the body. The pliable material is then converted to a non-pliable material by heat treating the pliable material under controlled conditions of temperature and time, thereby forming the desired orthotic member contoured to the body. The contoured orthotic member is further provided with a coating covering the non-pliable material, wherein the coating material has cushioning properties.

23 Claims, 5 Drawing Sheets

METHOD OF FORMING A CONTOURED ORTHOTIC MEMBER

TECHNICAL FIELD

The present invention relates generally to orthotics, and more particularly to a method of forming an orthotic member conforming to a contour of a body.

BACKGROUND OF THE INVENTION

Orthopedic braces are worn on the body of a user to support and stabilize a skeletal joint that has been weakened by injury or other infirmity. Orthopedic braces commonly employ orthotic members defined herein as the rigid structural components of the brace engaging or aligning with the body of the user in support thereof. The orthotic members are preferably shaped in correspondence with the contours of the body to enhance the fit of the brace to the body and, thus, to enhance the effectiveness of the brace for its desired function. Typically, the rigid orthotic members are dynamically linked together by one or more hinges enabling controlled pivotal movement of the joint during rehabilitative therapy or user activity while wearing the orthopedic brace. The orthopedic brace is positioned on the body such that the hinges traverse the joint being stabilized, while the orthotic members are secured to the body at a plurality of engagement faces above and below the joint.

Because orthopedic braces are commonly worn by athletes and other participants in active endeavors, orthopedic braces, and in particular the orthotic members thereof, are desirably designed to be lightweight, yet substantially resistant to structural deformation or failure. In addition, the orthotic members are desirably designed to have smooth surfaces free of protruding components, thereby avoiding injury or irritation to the user of the orthopedic brace as well as to others coming in contact with the orthopedic brace. In an effort to satisfy these performance requirements, orthotic members of conventional braces are generally formed from either metallic materials, such as metals or metal alloys, or non-metallic synthetic materials, such as plastics or fibrous composites. Although orthotic members formed from either type of material generally perform satisfactorily, a number of tradeoffs are associated with the selection of one type of material over the other for use in orthotic members. For example, conventional synthetic materials are extremely costly relative to metallic materials. In addition, fabrication of orthotic members from synthetic materials is relatively more complex and labor intensive than fabrication from metallic materials because synthetic materials are typically fabricated into orthotic members using a combination of hand layup and custom molding processes requiring a relatively high level of technical knowledge and skill, whereas metal materials are typically fabricated into orthotic members using well established low technology processes. Accordingly, fabrication costs for orthotic members formed from synthetic materials are substantially higher relative to fabrication costs for corresponding orthotic members formed from metallic materials.

The use of metallic materials in the fabrication of orthotic members has still further advantages relative to synthetic materials. In general, metallic materials are more ductile and less brittle than synthetic materials. Consequently, orthotic members fabricated from metallic materials have superior performance characteristics when used in orthopedic braces that are subjected to significant stresses from highly active endeavors such as athletics. Under these conditions, synthetic materials will often fracture rendering the orthotic member useless, whereas metallic materials tend to survive the same stresses and continue to function. In addition, the configuration of orthotic members formed from metallic materials can be modified to some extent after fabrication by applying sufficient force thereto, if desired, whereas the configuration of orthotic members formed from synthetic materials is essentially fixed after fabrication. Thus, for example, orthotic members formed from metallic materials can be conformed to changes in the dimensions of a body that occur over time, such as when swelling from an injury diminishes as the injury heals to reduce the dimensions of the body at the point of the injury.

Synthetic materials offer some critical advantages over metallic materials when used in the fabrication of orthotic members. Most body contours such as contours of the limbs, to which orthopedic members are fitted, are long sweeping arcs. Synthetic materials are well suited for conforming to these contours. They can accurately be molded into complex configurations and retain complex configurations with a high degree of performance.

Conversely, the characteristics that make some metallic materials desirable in an orthotic member, such as high tensile strength and elasticity, are the same characteristics that make it difficult to fabricate an orthotic member with long sweeping bends from metallic material. Although the metal can be bent into the desired shape, once the bending forces are removed, the metal will tend to spring back toward its original configuration. Typically this is overcome by configuring the orthotic member with relatively tight bends. Although tight bends tend to retain their shape, they do not conform well to body contours. It is apparent from the foregoing that a need continues to exist for orthotic members that avoid the inherent shortcomings of conventional orthotic members. In particular, a need exists for lightweight orthotic members that retain sufficient strength and durability to substantially resist deformation or failure during use of an orthopedic brace employing the orthotic members. A need further exists for orthotic members satisfying these performance requirements that can be produced at less cost, particularly with respect to materials and fabrication methods, in response to cost sensitivities in the health care industry.

Accordingly, it is an object of the present invention to provide a method of forming a contoured orthotic member that has enhanced performance characteristics when employed in an orthopedic brace. More particularly, it is an object of the present invention to provide a method of forming a contoured orthotic member for an orthopedic brace, wherein the orthotic member is relatively lightweight. It is another object of the present invention to provide a method of forming a contoured orthotic member for an orthopedic brace, wherein the orthotic member is relatively resistant to structural deformation or failure. It is still another object of the present invention to provide a method of forming a contoured orthotic member for an orthopedic brace, wherein the orthotic member substantially permanently conforms to the contours of a body on which it is mounted. It is yet another object of the present invention to provide a method of forming a contoured orthotic member for an orthopedic brace, wherein the orthotic member is relatively safe and comfortable to the user and others coming in contact with the orthotic member. It is a further object of the present invention to provide a method of forming a contoured orthotic member for an orthopedic brace, wherein the orthotic member is relatively durable. It is still a further object of the present invention to provide a method of forming a contoured orthotic member for an orthopedic brace, wherein the method substantially reduces material and fabrication costs, thereby reducing the overall cost of the associated orthopedic brace. These objects and others are achieved by the present invention described hereafter.

SUMMARY OF THE INVENTION

The present invention is a method of forming an orthotic member conforming to a contour of a body. A flat member is initially provided having a substantially two-dimensional shape and constructed from a pliable material. A preferred means of obtaining the flat member is to stamp it from a sheet of the pliable material. The flat member is then bent into a substantially three-dimensional shape approximating the contour of the body. A preferred means of bending the flat member in correspondence with the contour of the body is to align the flat member with a three-dimensional form having a pattern approximating the contour of the body indented in the surface of the form. The flat member is then bent onto the pattern resulting in a three-dimensional member. The pliable material of the three-dimensional member is converted to a non-pliable material thereafter, forming the desired orthotic member contoured to the body. A preferred means of converting the pliable material to a non-pliable material is to heat treat the pliable material, sequentially heating and quenching the pliable material under controlled conditions of temperature and time. The contoured orthotic member can further be provided with a coating covering the non-pliable material, wherein the coating material has cushioning properties.

The present invention will be further understood, both as to its structure and operation, from the accompanying drawings, taken in conjunction with the accompanying description, in which similar reference characters refer to similar parts.

DESCRIPTION OF PREFERRED EMBODIMENTS

Figure 1:
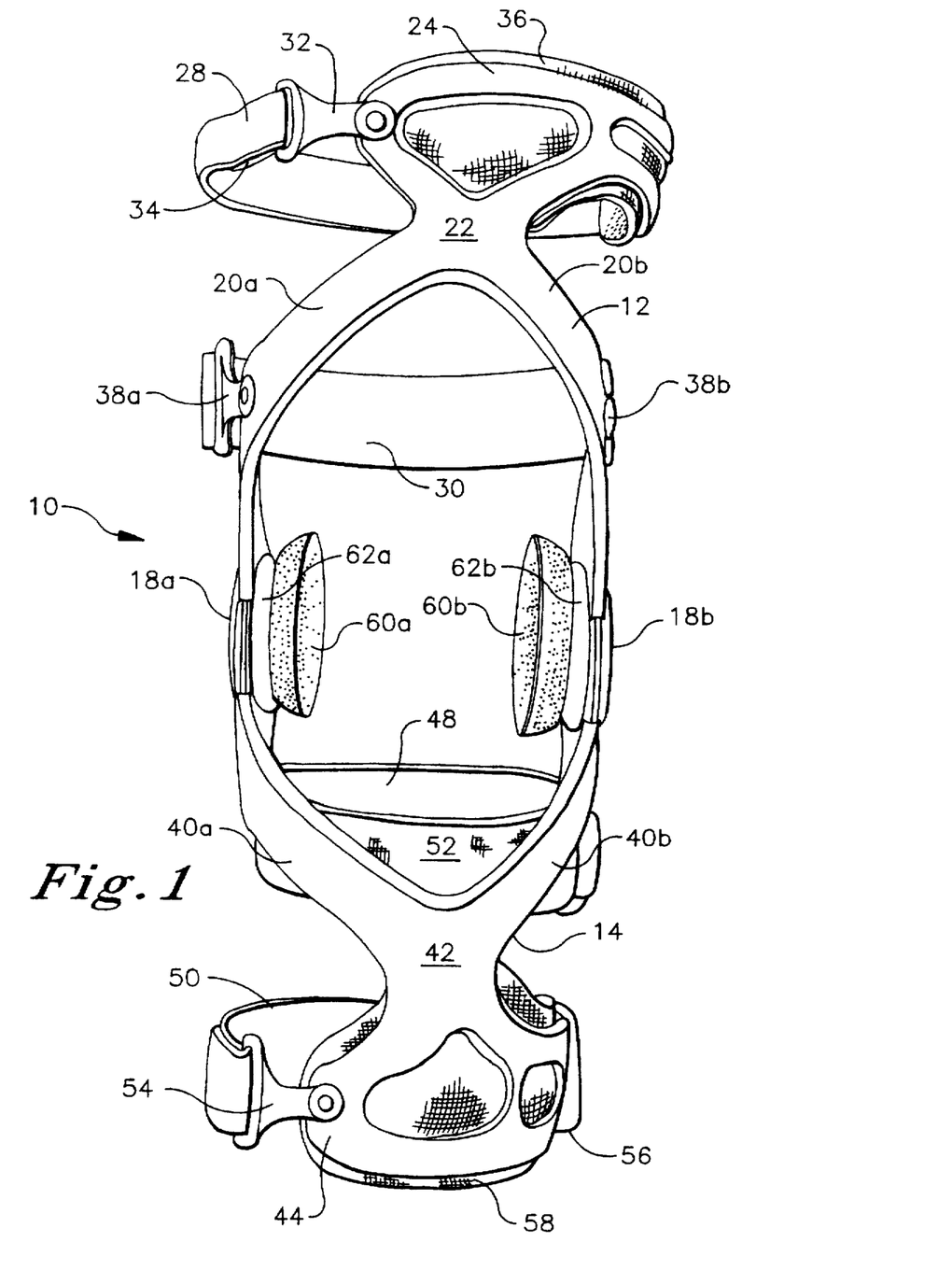
FIG. 1 is a front perspective view of an orthopedic brace incorporating orthotic members formed in accordance with the method of the present invention.
Figure 2:
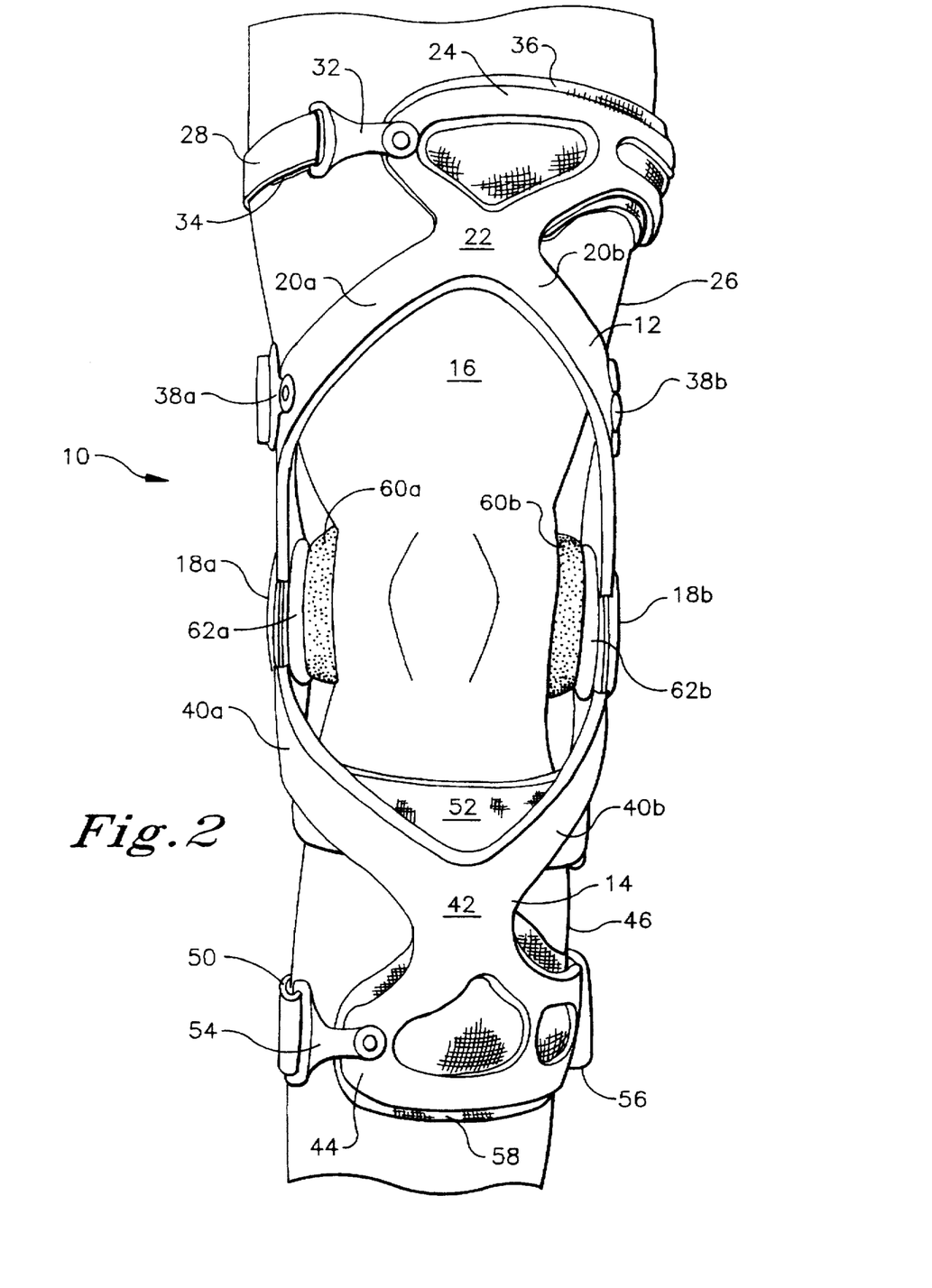
FIG. 2 is a front perspective view of the orthopedic brace of FIG. 1 mounted on the leg of a user.

Referring initially to FIGS. 1 and 2, an orthopedic brace, having contoured orthotic members formed in accordance with the method of the present invention described hereafter, is generally designated 10. For purposes of illustration, the orthopedic brace 10 shown and described herein is a knee brace having first and second contoured orthotic members mountable 12, 14 on the left leg 16 of a human body. It is understood, however, that the present invention is not limited to the specific configurations of the orthopedic brace 10 and contoured orthotic members 12, 14. The skilled artisan can readily adapt the instant teaching to form contoured orthotic members and associated orthopedic braces that are configured for mounting on the opposite leg or other joints of the body within the scope of the present invention.

The first and second contoured orthotic members 12, 14 of the orthopedic brace 10 are rotationally positioned about a medial hinge 18a and a lateral hinge 18b. Exemplary medial and lateral hinges 18a, 18b having utility herein are described in our copending U.S. patent application entitled "Hinge for an Orthopedic Brace", Ser. No. 08/656,088, filed on May 31, 1996, and incorporated herein by reference. The first contoured orthotic member 12 is more specifically termed the upper brace assembly in recognition of its unitary construction, integrating the entire rigid support structure of the orthopedic brace 10 above the hinges, 18a, 18b in a single element aligning with the upper leg. The second contoured orthotic member 14 is likewise more specifically termed the lower brace assembly, integrating the entire rigid support structure of the orthopedic brace 10 below the hinges 18a, 18b in a single element aligning with the lower leg.

The upper brace assembly 12 includes an upper medial arm 20a and an upper lateral arm 20b, each having a lower proximate end rotatably coupled by the medial and lateral hinges 18a, 18b, respectively. The upper medial and lateral arms 20a, 20b arc in an upwardly anterior direction to form a first upper anterior cross member 22. The upper brace assembly 12 also includes a second upper anterior cross member 24 located above the first upper anterior cross member 22. The upper brace assembly 12 extends substantially the length of the upper leg 26 of the user and is retained in removable engagement with the upper leg 26 by means of first and second upper adjustable straps 28, 30. The first upper adjustable strap 28 includes a pivotable loop fixture 32 rotatably anchored to the second upper anterior cross member 24. A self-connecting strap end 34 is threaded through the pivotable loop fixture 32 and connected to itself. An anterior pad 36 provides a cushion between the upper anterior cross members 22, 24 and the anterior of the user's upper leg 26. The second upper adjustable strap 30 engages the upper medial and lateral arms 20a, 20b below the first upper adjustable strap 28 and includes pivotable loop fixtures 38a, 38b.

The lower brace assembly 14 includes a lower medial arm 40a and a lower lateral arm 40b, each having an upper proximate end rotatably coupled by the medial and lateral hinges 18a, 18b, respectively. The lower medial and lateral arms 40a, 40b arc in a downwardly anterior direction to form a first lower anterior cross member 42. The lower brace assembly 14 also includes a second lower anterior cross member 44 located below the first lower anterior cross member 42. The lower brace assembly 14 extends substantially the length of the lower leg 46 of the user and is retained in removable engagement with the lower leg 46 by means of first and second lower adjustable straps 48, 50. The first lower adjustable strap 48 engages the lower medial and lateral arms 40a, 40b above the second lower adjustable strap 50 and includes an anterior pad 52. The second lower adjustable strap 42 includes a pivotable loop fixture 54 rotatably anchored to the second lower anterior cross member 44. A self-connecting strap end 56 is threaded through the pivotable loop fixture 54 and connected to itself. An anterior pad 58 provides a cushion between the lower anterior cross members 42, 44 and the anterior portion of the user's lower leg 46.

As noted above, the lower adjustable straps 48, 50 attach the lower brace assembly 14 to the user's lower leg 46 and the upper adjustable straps 28, 30 attach the upper brace assembly 12 to the user's upper leg 26. Medial and lateral hinge pads 60a, 60b retained by medial and lateral hinge pad holders 62a, 62b are further provided to cushion the user's medial and lateral knee condyles 64a, 64b from the hinges 18a, 18b.

The method of the present invention is initially described with reference to FIG. 3, wherein a two-dimensional flat member is shown and generally designated 66. The flat member 66 is the predecessor to the three-dimensional first contoured orthotic member 12 formed in accordance with the method of the present invention. The flat member 66 is fabricated from a relatively soft, pliable, malleable material that is readily deformable to a three-dimensional contoured shape by bending, either manually or mechanically. The material from which the flat member 66 is fabricated is further characterized as being capable of conversion to a relatively hardened, non-pliable, non-malleable material that is substantially resistant to deformation when subjected to the normal physical stresses of an orthopedic brace. Conversion of the pliable material to a non-pliable material is preferably effected by a heat treatment, wherein the material is heated and quenched in a manner that tempers the material, rendering it non-pliable. A material satisfying the above-recited criteria is typically a heat-treatable metallic material defined herein as any composition made up primarily of a pure metal, a metal alloy, or a combination thereof that is rendered substantially harder and less pliable when subjected to sequential heating and quenching under conditions within the purview of the skilled artisan. The heat treatable metallic material is preferably a heat-treatable metal alloy, more preferably a heat-treatable metal alloy selected from the group consisting of aluminum alloys and titanium alloys, and most preferably a heat-treatable metal alloy of aluminum.

The flat member 66 can be fabricated in substantially any manner apparent to the skilled artisan. In a preferred embodiment, the flat member 66 is fabricated by stamping the outline of the flat member 66 from a flat sheet (not shown) of the selected pliable material. The configuration of the flat member 66 is augmented with a number of features during fabrication thereof. In particular, a plurality of fully-enclosed openings or cut-outs are stamped into the flat member 66, including areal openings 68, 70 provided between the first and second upper anterior cross members 22, 24 to reduce the weight of the flat member 66, and correspondingly to reduce the weight of the first contoured orthotic member 12 formed therefrom. Rivet apertures 72a, 72b, 72c are stamped into the second upper anterior cross member 24, upper medial arm 20a, and upper lateral arm 20b, respectively, to receive rivets securing the pivotal loop fixtures 32, 38a, 38b to the first contoured orthotic member 12. Hinge apertures 74a, 74b are stamped into the ends of the upper medial arm 20a and upper lateral arm 20b, respectively, to receive the medial and lateral hinges 18a, 18b rotatably connecting the first contoured orthotic member 12 to the second contoured orthotic member 14. In addition, a plurality of teeth 76 are stamped into the ends of the upper medial and lateral arms 20a, 20b to integrally cooperate with the medial and lateral hinges 18a, 18b. Finally, a strap slot 78 is stamped into the second upper anterior cross member 24 opposite the rivet aperture 72a to receive and anchor the first upper adjustable strap 28.

Figure 4:
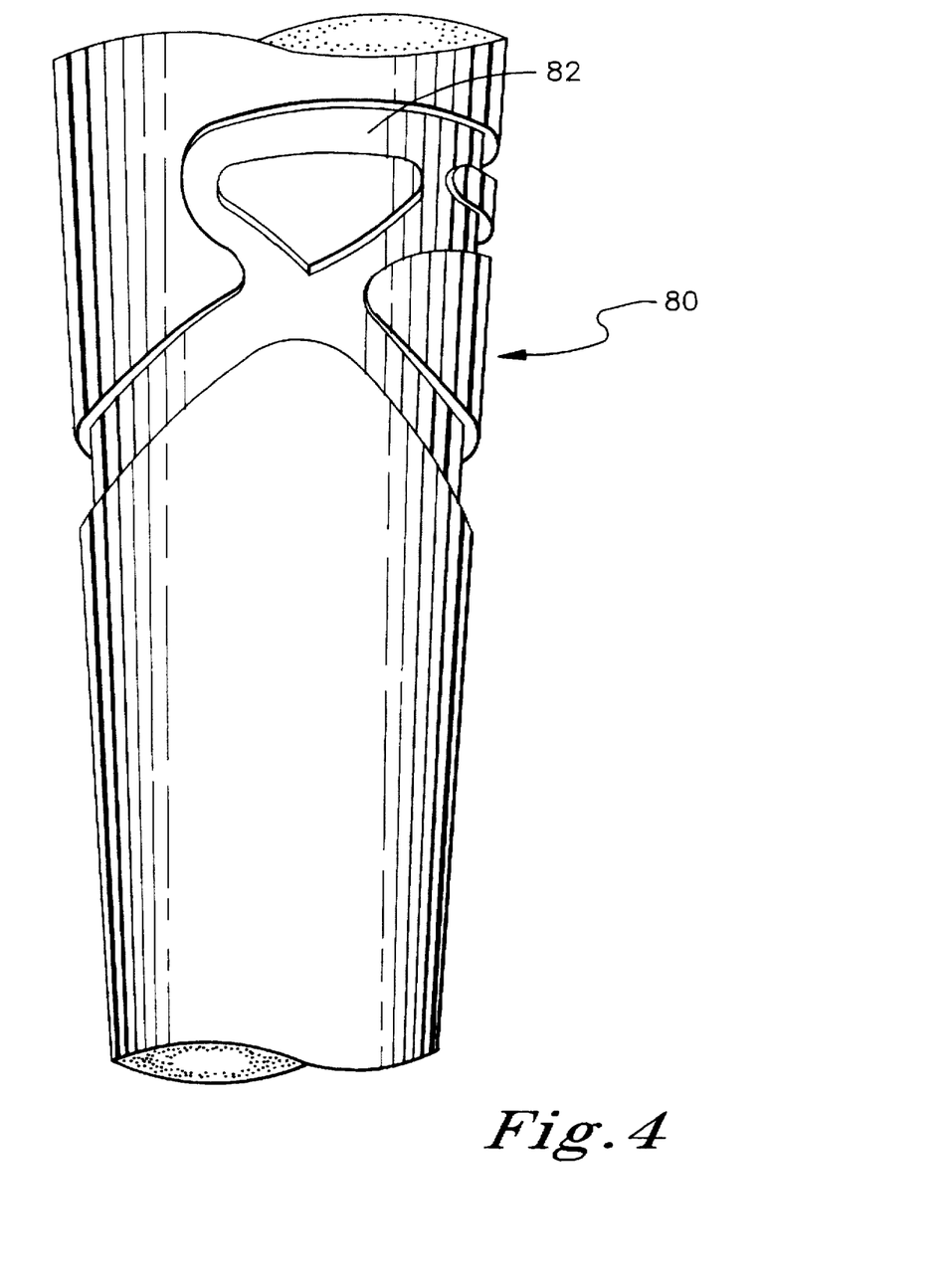
FIG. 4 is a front perspective view of a form used to shape a three-dimensional member from the two-dimensional flat member of FIG. 3 in accordance with the method of the present invention.

Referring to FIG. 4, the method of the present invention further comprises positioning the flat member 66 onto a form 80, such as a mandrel, having a three-dimensional pattern 82 in the desired shape of the first contoured orthotic member 12. The pattern 82 is etched, carved, or otherwise indented in the surface of the form 80. The form 80 approximates the shape of a contoured portion of the body that the first contoured orthotic member 12 is to engage when mounted on the body. Thus, in the present illustration, the form 80 is configured in the shape of a conic section approximating the shape of the upper leg 26. It is apparent to the skilled artisan that different sized forms and correspondingly different sized flat members can be employed to fabricate different sized orthotic members for various users having different sized bodies in accordance with the method of the present invention.

The flat member 66 is preferably positioned onto the form by aligning a point on the flat member 66, such as, for example, the midpoint of the first upper anterior cross member 22, with a corresponding point on the three-dimensional pattern 82 and coupling the aligned points of the flat member 66 and pattern 82. The flat member 66 is then progressively bent down into the pattern 82 about the aligned points until the flat member 66 is converted to a three-dimensional member that is shaped in identical conformance with the indentation of the pattern 82 on the form 60. As such, the three-dimensional member correspondingly conforms identically to the desired shape of the first contoured orthotic member 12, as shown with reference to FIG. 5. Bending the flat member 66 is preferably accomplished by manual means, such as by hand or with a hammer or other hand tool, but bending can alternatively be accomplished by mechanical means, such as by a mechanized tool.

The method of forming the first contoured orthotic member 12 further comprises treating the three-dimensional member to convert the material thereof from the relatively soft, pliable, deformable material to a relatively rigid, non-pliable, deformation-resistant material. The conversion treatment also renders the three-dimensional member resistant to springing back to the shape of the flat member 66. Accordingly, the conversion treatment effectively enables the first contoured orthotic member 12 to substantially permanently retain its three-dimensional shape. A heat treatment is the preferred conversion treatment, whereby the three-dimensional member is heated and subsequently quenched under controlled conditions. In particular, the three-dimensional member is heated at a predetermined rate to a predetermined high temperature substantially exceeding ambient temperature for a predetermined time period and then quenched at a predetermined rate for a predetermined time period to a predetermined low temperature. Heating is preferably performed in a conventional radiant or convective heating device such as an oven. Quenching is preferably performed by mist spraying or liquid immersion. The precise values of heating and quenching temperatures, times, and rates are predetermined as a function of the actual metallic material being treated and the degree of treatment desired. Determination of these values is readily within the purview of the skilled artisan for substantially any conventional heat-treatable metallic material.

Although the metallic material from which the orthotic member is to be formed is essentially pliable at this stage, the material typically exhibits some spring back. Therefore, it is preferable to securably position a retainer 84, as shown with reference to FIG. 6, between the ends of the upper medial and lateral arms 20 a, 20b after shaping the three-dimensional member until completion of the conversion treatment. When positioned in the present manner, the retainer 84 fixes the alignment of the upper medial and lateral arms 20a, 20b, and correspondingly the alignment of the hinge apertures 74a, 74b, and prevents the upper medial and lateral arms 20a, 20b from springing back to some degree. Once the conversion treatment has been performed, the resulting first contoured orthotic member 12 assumes a relaxed condition that is substantially resistant to springing back upon removal of the retainer 84. Precise alignment of the upper medial and lateral arms 20a, 20b and the hinge apertures 74a, 74b is substantially permanently retained thereafter, which is critical to proper rotational operation of the orthopedic brace 10 employing the first and second contoured orthotic members 12, 14.

Figure 6:
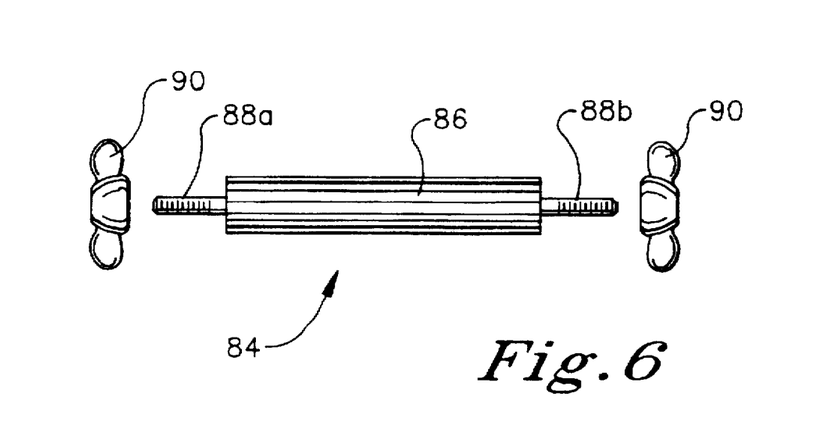
FIG. 6 is a front exploded view of retainer employed in accordance with the method of the present invention.

The retainer 84 comprises a thickened midsection 86, preferably a high-strength rigid metal rod that is substantially non-pliable relative to the pliable material, having a length equal to the distance between the hinge apertures 74a, 74b and a diameter greater than the diameter of the hinge apertures 74a, 74b. Threaded extensions 88a, 88b are provided on opposite ends of the midsection 86, wherein the threaded extensions 88a, 88b each have a diameter less than the diameter of the hinge apertures 74a, 74b and a length greater than the thickness of the upper medial and lateral arms 20a, 20b. As such, the threaded extensions 88a, 88b are received by the hinge apertures 74a, 74b and extend therethrough. Each threaded extension 88a, 88b is provided with a conventional fastener, such as a wing nut 90, that enables the threaded extensions 88a, 88b to be selectively secured in the hinge apertures 74a, 74b, while the midsection 86 maintains the distance therebetween.

Figure 5:
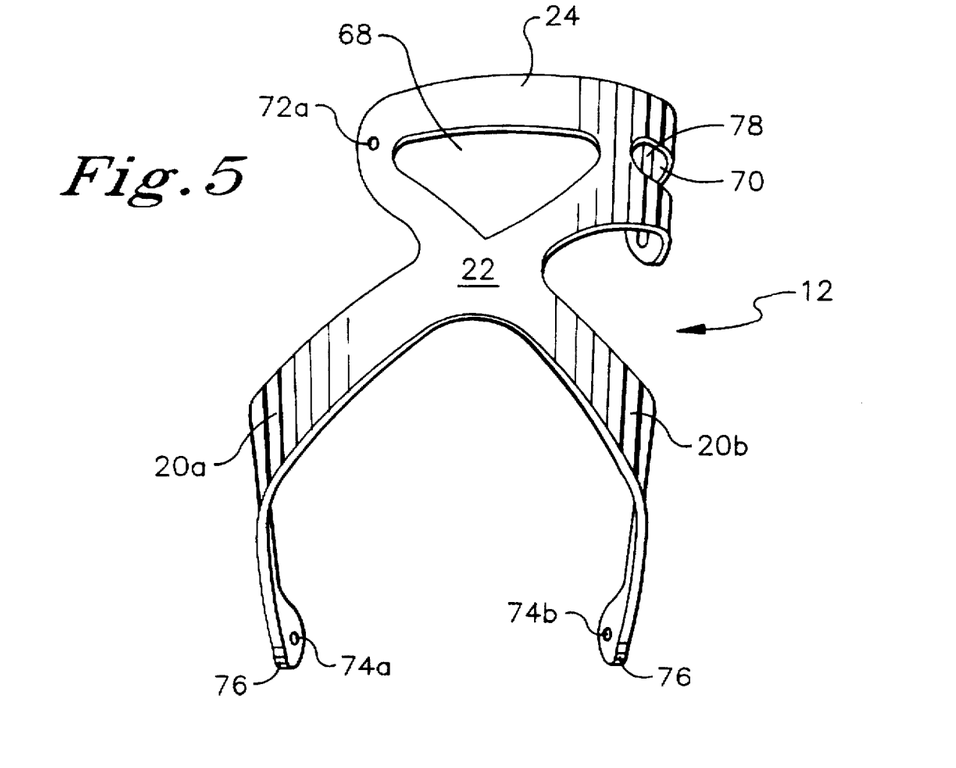
FIG. 5 is a front perspective view of the three-dimensional orthotic member formed from the two-dimensional flat member of FIG. 3 in accordance with the method of the present invention.

Referring to FIG. 5, the first contoured orthotic member 12 is shown formed from a relatively rigid, non-pliable, deformation-resistant material and having a three dimensional shape substantially conforming to the shape of a contoured portion of the body. The final step in the method of the present invention is to enclose the first contoured orthotic member 12 in a coating that cushions the user and others from the exterior surface of the treated material of the first contoured orthotic member 12. The coating is preferably a relatively thin layer of a coating material that conforms to the contours of the first orthotic member 12. The coating material is preferably softer and smoother edged than the treated metallic material of the first contoured orthotic member 12. The coating of the first contoured orthotic member 12 functions to enhance the comfort of the user of the orthopedic brace 10 as well as to enhance the comfort of others coming into contact with the orthopedic brace 10. A preferred material of the coating satisfying the above-recited performance criteria is a plastic, and more preferably a vinyl or plastisol.

The coating is applied to the first contoured orthotic member 12 by substantially any conventional means. A preferred means of applying the coating, however, comprises preparing a liquid bath of a heat-curable coating material at ambient temperature. The first contoured orthotic member 12 is heated to a temperature substantially greater than ambient temperature and then dipped into the liquid bath to fully immerse the first contoured orthotic member 12 in the coating material. The hot first orthotic member 12 partially cures the coating material coming into contact with the first orthotic member, causing adherence of the coating material thereto. The first orthotic member 12 is then withdrawn from the bath and placed in a heated oven to completely cure the coating material, thereby obtaining the finished product, i.e., the coated first contoured orthotic member 12. The above-described means of applying the coating to the first orthotic member 12 is advantageous because it enables the coating to conform to complex three-dimensional shapes and to surfaces having fully-enclosed openings formed therein.

Although not described herein, it is understood that the second contoured orthotic member 14 of the orthopedic brace 10 is formed in substantially the same manner as described above with respect to the first contoured orthotic member 12. The following examples demonstrate the practice and utility of the present invention, but are not to be construed as limiting the scope thereof.

Example 1

Figure 3:
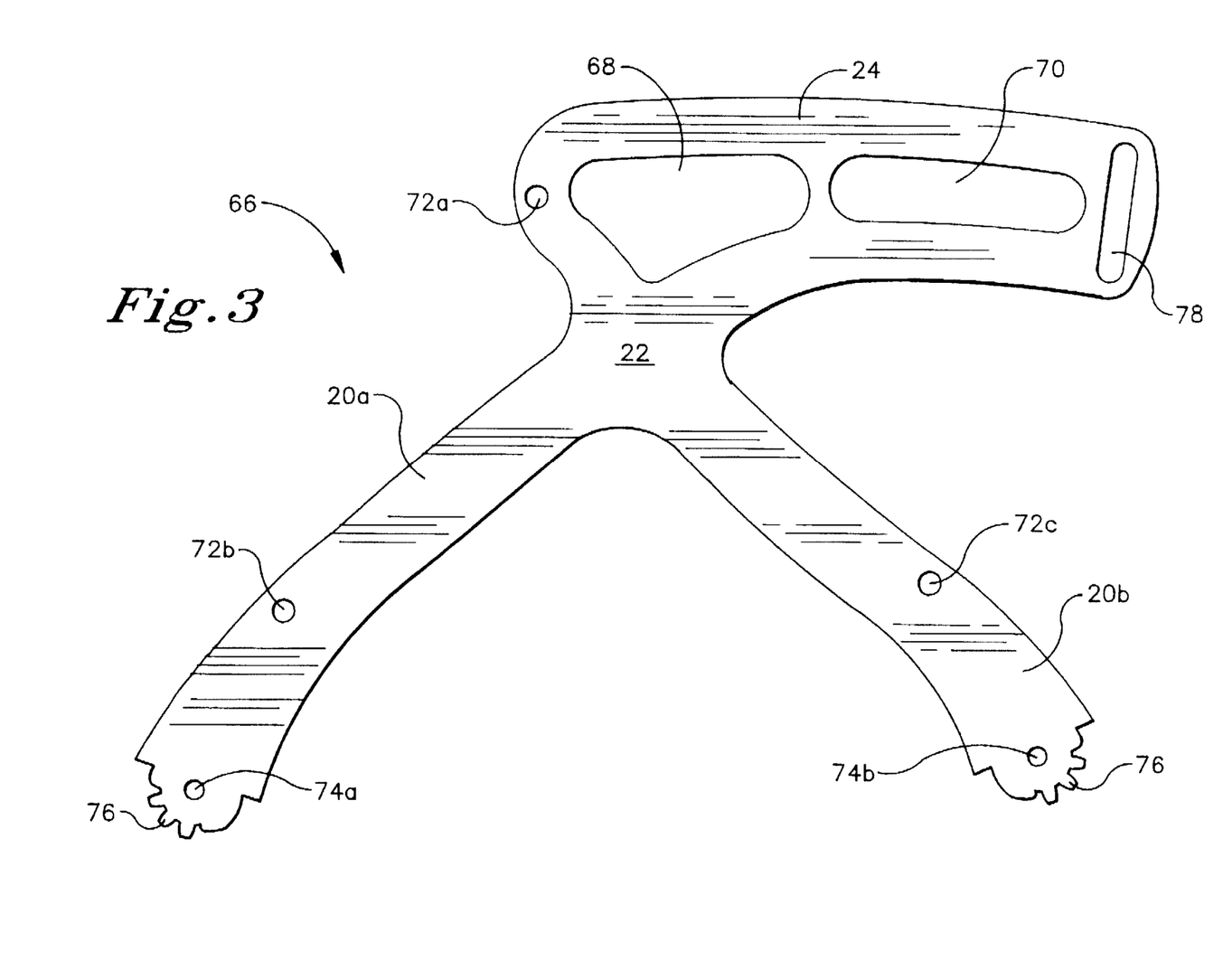
FIG. 3 is a front view of a two-dimensional flat member prior to formation of a three-dimensional orthotic member therefrom in accordance with the method of the present invention.

A flat sheet of 6061 aluminum alloy in an "O" (soft) condition of pliability is provided, from which a two-dimensional flat member is stamped having substantially the same configuration as shown in FIG. 3. The two-dimensional flat member is bent onto a three-dimensional pattern of a form to produce a three-dimensional member having substantially the same configuration as shown in FIG. 5. A retainer is affixed to the three-dimensional member and the fixtured three-dimensional member is placed in an oven where it is heated at a temperature of 985° F. for 1 hour. The three-dimensional member is withdrawn from the oven and immediately quenched by mist spraying. The retainer is removed to obtain the contoured orthotic member in a T4 condition of hardness. The orthotic member is substantially non-pliable, having a tensile strength of 35,000 psi and a yield strength of 21,000 psi.

Example 2

An orthotic member is produced in substantially the same manner as Example 1. However, following heat treatment of the three-dimensional member to a T4 condition, the member is artificially aged by continued heating in an oven at a temperature of 320° F. for 18 hours. The resulting orthotic member is in a T6 condition, having a tensile strength of 45,000 psi and a yield strength of 40,000 psi.

It is understood that other configurations of contoured orthotic members not shown herein can also be formed in accordance with the present method and fall within the scope of the present invention. Thus, while the foregoing embodiment of the invention have been described and shown, it is further understood that alternatives and modifications, such as those suggested and others, may be made thereto and fall within the scope of the present invention.

We claim:

1. A method of forming an orthotic member conforming to a contour of a body comprising:

providing a flat member, wherein said flat member has a substantially two-dimensional shape and is constructed from a pliable metallic material;

bending said flat member at an ambient temperature into a substantially three-dimensional shape on a form having a pattern approximating a contour of a body, wherein said substantially three-dimensional shape corresponds to said contour; and performing a heat treating procedure on said pliable metallic material said heat treating procedure including heating said pliable metallic material having said substantially three-dimensional shape to a relatively higher temperature substantially exceeding said ambient temperature to convert said pliable metallic material to a non-pliable metallic material forming said orthotic member contoured to said body, wherein said orthotic member has said three-dimensional shape and is constructed from said non-pliable metallic material.

2. The method of claim 1 further comprising stamping said flat member from a sheet of said pliable metallic material.

3. The method of claim 1 wherein said pliable metallic material is an aluminum alloy.

4. The method of claim 1 wherein said heat treating procedure further includes quenching said pliable metallic material to a relatively lower temperature substantially below said relatively higher temperature after heating said pliable metallic material.

5. The method of claim 1 further comprising coating said non-pliable metallic material of said orthotic member with a coating material, wherein said coating material is substantially softer than said non-pliable metallic material.

6. The method of claim 5 wherein said orthotic member is coated with said coating material by dipping said orthotic member in a liquid bath of said coating material and curing said coating material on said orthotic member to a solid.

7. The method of claim 5 wherein said coating material is a plastic.

8. The method of claim 1 further comprising securing a relatively non-pliable retaining member to said pliable metallic material having said three-dimensional shape during said heat treating procedure to maintain said three-dimensional shape while said pliable metallic material is converted to said non-pliable metallic material.

9. The method of claim 1 wherein said flat member has a continuous metal construction.

10. A method of forming an orthotic member conforming to a contour of a body comprising:

providing a flat member, wherein said flat member has a substantially two-dimensional shape and is constructed from a pliable metallic material;

bending said flat member at an ambient temperature into a substantially three-dimensional shape approximating a contour of a body; and converting said pliable metallic material to a non-pliable metallic material to form said orthotic member contoured to said body, wherein said orthotic member has said three-dimensional shape and is constructed from said non-pliable metallic material.

11. The method of claim 10 wherein said flat member is bent on a form having a pattern approximating said contour.

12. The method of claim 10 further comprising stamping said flat member from a sheet of said pliable metallic material.

13. The method of claim 10 wherein said pliable metallic material is an aluminum alloy.

14. The method of claim 10 wherein said pliable metallic material is converted to said non-pliable metallic material by performing a heat treating procedure on said pliable metallic material, said heat treating procedure comprising heating said pliable metallic material to a relatively higher temperature exceeding said ambient temperature and quenching said pliable metallic material to a relatively lower temperature.

15. The method of claim 14 further comprising securing a relatively non-pliable retaining member to said pliable metallic material having said three-dimensional shape during said heat treating procedure to maintain said three-dimensional shape while said pliable metallic material is converted to said non-pliable metallic material.

16. The method of claim 10 further comprising coating said non-pliable metallic material of said orthotic member with a coating material, wherein said coating material is substantially softer than said non-pliable metallic material.

17. The method of claim 16 wherein said coating material is a plastic and said orthotic member is coated with said coating material by dipping said orthotic member in a liquid bath of said coating material and curing said coating material on said orthotic member to a solid.

18. A method of forming an orthotic member conforming to a contour of a body comprising:

providing a flat member formed from a pliable metallic material, wherein said flat member has a substantially two-dimensional shape and has a continuous metal construction;

bending said flat member into a substantially three-dimensional shape approximating a contour of a body; and converting said pliable metallic material to a non-pliable metallic material to form said orthotic member contoured to said body, wherein said orthotic member has said three-dimensional shape and is constructed from said non-pliable metallic material.

19. The method of claim 18 wherein said pliable material is converted to said non-pliable material by performing a heat treating procedure on said pliable metallic material.

20. The method of claim 19 wherein said heat treating procedure comprises heating said pliable metallic material to a relatively higher temperature exceeding an ambient temperature of said bending step and quenching said pliable metallic material to a relatively lower temperature.

21. The method of claim 19 further comprising securing a relatively non-pliable retaining member to said pliable metallic material having said three-dimensional shape during said heat treating procedure to maintain said three-dimension shape while said pliable metallic material is converted to said non-pliable metallic material.

22. The method of claim 18 further comprising coating said non-pliable metallic material of said orthotic member with a coating material, wherein said coating material is substantially softer than said non-pliable metallic material.

23. The method of claim 22 wherein said orthotic member is coated with said coating material by dipping said orthotic member in a liquid bath of said coating material and curing said coating material on said orthotic member to a solid.

* * * * *